United States Patent
Ikeo et al.

(10) Patent No.: US 10,280,437 B2
(45) Date of Patent: May 7, 2019

(54) METHOD FOR PRODUCING ETHANOL

(71) Applicant: JGC CORPORATION, Tokyo (JP)

(72) Inventors: Makoto Ikeo, Ibaraki (JP); Shohei Okino, Ibaraki (JP)

(73) Assignee: JGC CORPORATION, Tokyo (JP)

( * ) Notice: Subject to any disclaimer, the term of this patent is extended or adjusted under 35 U.S.C. 154(b) by 0 days.

(21) Appl. No.: 15/102,517

(22) PCT Filed: Dec. 12, 2013

(86) PCT No.: PCT/JP2013/083316
§ 371 (c)(1),
(2) Date: Jun. 7, 2016

(87) PCT Pub. No.: WO2015/087422
PCT Pub. Date: Jun. 18, 2015

(65) Prior Publication Data
US 2016/0376611 A1   Dec. 29, 2016

(51) Int. Cl.
*C12P 7/06*      (2006.01)
*C12P 7/10*      (2006.01)

(52) U.S. Cl.
CPC .............. *C12P 7/10* (2013.01); *C12P 7/06* (2013.01); *Y02E 50/16* (2013.01); *Y02E 50/17* (2013.01)

(58) Field of Classification Search
None
See application file for complete search history.

(56) References Cited

U.S. PATENT DOCUMENTS 8,765,427 B2 *  7/2014  Murata ................... C12P 7/06
                                                   435/162
9,416,375 B2 *  8/2016  Fernholz .............. A01N 37/16

FOREIGN PATENT DOCUMENTS

JP   2012-205988    10/2012
WO   2012005246     1/2012
WO   2013005595     1/2013

OTHER PUBLICATIONS

Sun et al. (Bioresource Tech., vol. 83, 2002, pp. 1-11).*
Palmqvist et al. (Bioresource Tech., vol. 74, 2000, pp. 25-33).*
Larsson et al. (Enzyme Microb. Technol., 1999, vol. 24, pp. 152-159).*
"International Search Report (Form PCT/ISA/210) of PCT/JP2013/083316", dated Mar. 11, 2014, with English translation thereof, pp. 1-4.
Lu et al., "Influence of High Solid Concentration on Enzymatic Hydrolysis and Fermentation of Steam-Exploded Corn Stover Biomass", Appl Biochem Biotechnol, Jul. 15, 2008, pp. 360-369.
Taherzadeh et al., "Acetic acid-friend or foe in anaerobic batch conversion of glucose to ethanol by *Saccharomyces cerevisiae*?", Chemical Engineering Science, Aug. 1997, pp. 2653-2659.
Peng et al., "Influence of furfural concentration on growth and ethanol yield of *Saccharomyces kluyveri*", Journal of Environmental Sciences, Jun. 5, 2007, pp. 1528-1532.

* cited by examiner

*Primary Examiner* — Hope Robinson
(74) *Attorney, Agent, or Firm* — JCIPRNET

(57) ABSTRACT

A method for producing ethanol, which is a method for producing ethanol from a saccharide obtained from biomass, includes a step of adding an additive solution containing at least acetic acid, formic acid, furfural, and hydroxymethylfurfural to the saccharide to prepare a mixed solution containing the saccharide and the additive solution, and a step of adding a microorganism to the mixed solution to ferment the saccharide using the microorganism, thereby producing ethanol.

2 Claims, 2 Drawing Sheets

METHOD FOR PRODUCING ETHANOL

CROSS-REFERENCE TO RELATED APPLICATION

This application is a 371 application of the international PCT application serial no. PCT/JP2013/083316, filed on Dec. 12, 2013. The entirety of each of the abovementioned patent applications is hereby incorporated by reference herein and made a part of this specification.

TECHNICAL FIELD

The present invention relates to a method for producing ethanol from saccharides obtained from biomass.

BACKGROUND ART

An example of methods for producing bioethanol using cellulose-based biomass as a raw material is an enzymatic ethanol production technique of producing a solution (hereafter referred to as a "saccharified solution") containing a saccharide containing glucose as a main component by enzymatically hydrolyzing at least one of cellulose and hemicellulose contained in cellulose-based biomass.

One of difficulties for putting the enzymatic ethanol production technique into practical use is to decrease the amount of an enzyme used. To decrease the amount of an enzyme used, the contact efficiency between the enzyme and at least one of cellulose and hemicellulose needs to be increased by performing a pretreatment for breaking the structure of biomass.

In the pretreatment for biomass, for example, water vapor, an acid, or an alkali is added to the biomass and heat and pressure are applied thereto. As a result of this pretreatment, lignin, cellulose, and hemicellulose in the biomass are degraded to produce organic acids and tars. These products (hereafter, may be referred to as "inhibitors") are generally known to inhibit an enzymatic saccharification reaction and a fermentation reaction in which saccharides obtained from biomass are converted into ethanol (e.g., refer to NPL 1).

Therefore, organic acids and the like are desirably removed by washing the biomass that has been subjected to a pretreatment in order to efficiently cause an enzymatic saccharification reaction.

CITATION LIST

Non Patent Literature

NPL 1: Lu, Y., et al., Influence of High Solid Concentration on Enzymatic Hydrolysis and Fermentation of Steam-Exploded Corn Stover Biomass. Applied Biochemistry and Biotechnology. 2010. 160(2): p. 360-369

SUMMARY OF INVENTION

Technical Problem

To efficiently cause an enzymatic saccharification reaction, organic acids and the like are desirably removed by washing the biomass that has been subjected to a pretreatment. However, the introduction of such a washing process increases the amount of liquid waste. This requires initial investment for liquid waste facilities and high cost for liquid waste treatment. Consequently, the cost is increased.

The following has been investigated to decrease the initial investment for liquid waste facilities and the cost for liquid waste treatment. That is, a plant (hereafter, referred to as a "cellulose-based ethanol plant") where ethanol is produced from cellulose-based biomass is established next to a plant where ethanol is produced from food biomass. By sharing these facilities, the initial investment for liquid waste facilities is decreased. However, the amount of liquid waste in the cellulose-based ethanol plant cannot be decreased by simply sharing the facilities.

In view of the foregoing, the present invention provides a method for producing ethanol in which the production efficiency of ethanol can be improved in a process for producing ethanol from a saccharide obtained from biomass.

Solution to Problem

A method for producing ethanol according to the present invention is a method for producing ethanol from a saccharide obtained from biomass, the method including a step of adding an additive solution containing at least acetic acid, formic acid, furfural, and hydroxymethylfurfural to the saccharide to prepare a mixed solution containing the saccharide and the additive solution, and a step of adding a microorganism to the mixed solution to ferment the saccharide using the microorganism, thereby producing ethanol.

In the method for producing ethanol according to the present invention, the additive solution may be a liquid waste produced by performing a steam explosion treatment or a dilute sulfuric acid treatment on the biomass.

In the method for producing ethanol according to the present invention, a total concentration of the acetic acid, the formic acid, the furfural, and the hydroxymethylfurfural contained in the mixed solution may be 400 ppm to 4500 ppm.

In the method for producing ethanol according to the present invention, the saccharide may be obtained by degrading at least one of cellulose and hemicellulose contained in the biomass by using at least one of an enzyme that degrades cellulose and an enzyme that degrades hemicellulose.

In the method for producing ethanol according to the present invention, the microorganism may be yeast.

Advantageous Effects of Invention

According to the present invention, the production efficiency of ethanol can be improved in a process for producing ethanol from a saccharide obtained from biomass.

DESCRIPTION OF EMBODIMENTS

Figure 1:
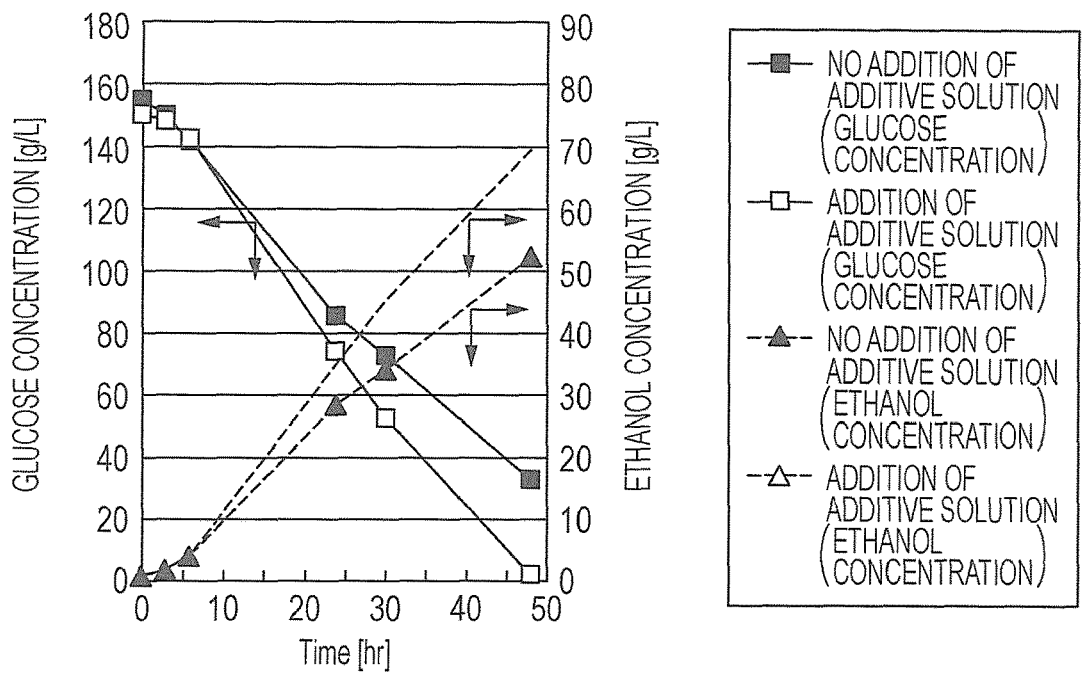
FIG. 1 is a graph illustrating the concentrations of glucose and ethanol contained in a mixed solution (aqueous solution), the concentrations being plotted against the time elapsed from the start of fermentation in a step of fermenting a saccharide containing glucose as a main component.

Embodiments of a method for producing ethanol according to the present invention will be described.

These embodiments are specifically described to facilitate the understanding of the spirit of the invention, and do not limit the present invention unless otherwise specified.

The method for producing ethanol according to this embodiment is a method for producing ethanol from a saccharide obtained from biomass, the method including a step of adding an additive solution containing at least acetic acid, formic acid, furfural, and hydroxymethylfurfural to the saccharide to prepare a mixed solution containing the saccharide and the additive solution, and a step of adding a microorganism to the mixed solution to ferment the saccharide using the microorganism, thereby producing ethanol.

First Embodiment

In this embodiment, the description will be made for the case where a saccharide is obtained by degrading at least one of cellulose and hemicellulose contained in biomass by using at least one of an enzyme that degrades cellulose and an enzyme that degrades hemicellulose.

In the method for producing ethanol according to this embodiment, first, biomass (wood, grass, or agricultural residues) is subjected to a pretreatment for improving the contact efficiency between at least one of cellulose and hemicellulose contained in the biomass and at least one of an enzyme that degrades cellulose and an enzyme that degrades hemicellulose.

Examples of the pretreatment include an alkali treatment, an organic solvent treatment, a steam explosion treatment, and a dilute sulfuric acid treatment for the biomass. From the viewpoint of enzymatic saccharification yield and equipment cost, a steam explosion treatment or a dilute sulfuric acid treatment is suitably employed.

A publicly known treatment is employed for the alkali treatment, organic solvent treatment, steam explosion treatment, or dilute sulfuric acid treatment for the biomass.

Then, a substance containing at least acetic acid, formic acid, furfural, and hydroxymethylfurfural is removed from the pretreated biomass.

For example, the following method is employed to remove the substance containing at least acetic acid, formic acid, furfural, and hydroxymethylfurfural from the pretreated biomass.

The substance containing at least acetic acid, formic acid, furfural, and hydroxymethylfurfural is removed from the pretreated biomass by heating the pretreated biomass using water at a temperature equal to or lower than the boiling point of water.

The treatment in which the pretreated biomass is heated using water at a temperature equal to or lower than the boiling point of water is believed to produce the following effects in addition to sufficient removal of components that inhibit saccharification with enzymes, such as a substance containing at least acetic acid, formic acid, furfural, and hydroxymethylfurfural left in the biomass. Examples of the effects include an effect of increasing an area in which an enzyme is in contact with cellulose by expanding the space between lignin and at least one of cellulose and hemicellulose and an effect of degrading and removing components that inhibit saccharification with enzymes and that are still left on the biomass not through simple adhesion but through a chemical bond with lignin as a result of incomplete degradation in the pretreatment.

As a result of the treatment through which the substance containing at least acetic acid, formic acid, furfural, and hydroxymethylfurfural is removed, the concentration of the substance containing at least acetic acid, formic acid, furfural, and hydroxymethylfurfural in the treated solution (solution containing water and biomass) increases. Therefore, after the completion of the treatment through which the substance containing at least acetic acid, formic acid, furfural, and hydroxymethylfurfural is removed, solid components are washed or neutralized to collect the biomass.

Subsequently, the pretreated biomass from which the substance containing at least acetic acid, formic acid, furfural, and hydroxymethylfurfural has been removed is dispersed in a solution (solvent) to prepare a slurry containing biomass (hereafter, may be referred to as a "biomass slurry").

The concentration of the biomass slurry, that is, the biomass content in the biomass slurry is appropriately controlled in accordance with, for example, the type of biomass and the pretreatment method. The biomass content is preferably 10 g to 30 g in 100 mL of the solution, that is, 10 w/v % to 30 w/v %.

An example of the solution (solvent) used for the biomass slurry is water.

An adsorption inhibitor is preferably added to the biomass slurry in order to prevent an enzyme (at least one of an enzyme that degrades cellulose and an enzyme that degrades hemicellulose) from being adsorbed onto lignin contained in the biomass (enzymatic adsorption).

Examples of the adsorption inhibitor include bovine serum albumin (BSA), cheese whey, and proteins derived from grain.

Subsequently, the biomass slurry and an appropriate amount of an aqueous solution (enzyme aqueous solution) containing at least one of an enzyme that degrades cellulose and an enzyme that degrades hemicellulose, which are suitable for degrading at least one of cellulose and hemicellulose contained in the biomass slurry, are charged into a reaction vessel to mix the biomass slurry and the enzyme aqueous solution (mixing step).

In this mixing step, the pH of the reaction vessel solution containing the biomass slurry and the enzyme aqueous solution is adjusted so that the pH condition is optimum for at least one of the enzyme that degrades cellulose and the enzyme that degrades hemicellulose used. Furthermore, the temperature of the reaction vessel is adjusted so that the temperature conditions are optimum for at least one of the enzyme that degrades cellulose and the enzyme that degrades hemicellulose used.

In this mixing step, the pH of the mixture containing the biomass slurry, the enzyme aqueous solution, and the additives is preferably adjusted so that at least one of the enzyme that degrades cellulose and the enzyme that degrades hemicellulose actively works. Specifically, the pH of the reaction-system aqueous solution is preferably adjusted to 4 to 6.

In this mixing step, the temperature of the mixture is preferably adjusted so that at least one of the enzyme that degrades cellulose and the enzyme that degrades hemicellulose actively works. Specifically, the temperature of the reaction system is preferably increased to 40° C. to 60° C.

Cellulase is used as an enzyme for degrading the biomass (at least one of the enzyme that degrades cellulose and the enzyme that degrades hemicellulose).

If a large amount of hemicellulose is contained in the biomass, xylanase or mannanase is preferably added as an enzyme for degrading hemicellulose (at least one of the enzyme that degrades cellulose and the enzyme that degrades hemicellulose), in addition to the cellulase.

The mixture containing the biomass slurry and the enzyme aqueous solution is stirred with a stirring blade or the like.

In this embodiment, the mixture is mixed by being gently stirred in the reaction vessel to the degree that the enzyme contained in the enzyme aqueous solution is not excessively deactivated. Thus, the biomass (at least one of cellulose and hemicellulose) is efficiently enzymatically saccharified to obtain a saccharide containing glucose as a main component (enzymatic saccharification reaction step).

In this enzymatic saccharification reaction step, the temperature of the mixture is preferably adjusted so that the enzyme actively works. Specifically, the temperature of the mixture is preferably kept at 40° C. to 60° C.

The enzymatic saccharification reaction step is performed until the saccharification of the biomass with the enzyme sufficiently proceeds and the reaction does not proceed any more. For example, the biomass is enzymatically degraded at 40° C. to 60° C. for about 2 to 20 days.

Subsequently, an additive solution containing at least acetic acid, formic acid, furfural, and hydroxymethylfurfural is added to the saccharide containing glucose as a main component to prepare a mixed solution containing the saccharide containing glucose as a main component and the additive solution (mixed solution-preparing step).

In this mixed solution-preparing step, the saccharide containing glucose as a main component and an appropriate amount of the additive solution containing at least acetic acid, formic acid, furfural, and hydroxymethylfurfural, the additive solution being suitable for fermentation of the saccharide containing glucose as a main component, are charged into a reaction vessel to mix the saccharide containing glucose as a main component and the additive solution.

The additive solution containing at least acetic acid, formic acid, furfural, and hydroxymethylfurfural is preferably a solution produced as a result of the pretreatment of the biomass and separated and removed from the pretreated biomass. The additive solution is more preferably a solution produced by performing a steam explosion treatment or a dilute sulfuric acid treatment on the biomass and separated and removed from the biomass that has been subjected to such a treatment.

The total concentration of the acetic acid, formic acid, furfural, and hydroxymethylfurfural contained in the mixed solution containing the saccharide containing glucose as a main component and the additive solution is preferably 400 ppm to 4500 ppm and more preferably 1000 ppm to 4500 ppm.

The saccharide containing glucose as a main component and the additive solution are stirred with a stirring blade or the like.

Subsequently, a microorganism was added to the mixed solution to ferment the saccharide containing glucose as a main component in the mixed solution using the microorganism, thereby producing ethanol (fermentation step).

In this fermentation step, the mixed solution and an appropriate amount of a microorganism suitable for fermentation of the saccharide containing glucose as a main component are charged into a reaction vessel to mix the mixed solution and the microorganism.

Examples of the microorganism include yeast, colon bacilli, *Zymomonas* and *Corynebacterium*.

The amount of the microorganism added to the mixed solution is preferably 0.1 to 3 parts by mass and more preferably 0.2 to 2.2 parts by mass when the amount of the saccharide containing glucose as a main component in the mixed solution is assumed to be 100 parts by mass.

The mixed solution and the microorganism are stirred with a stirring blade or the like.

In this fermentation step, the temperature of the mixture containing the microorganism is preferably adjusted so that the microorganism actively works. Specifically, the temperature is preferably kept at 30° C. to 38° C.

The fermentation step is performed until the fermentation of the saccharide containing glucose as a main component with the microorganism sufficiently proceeds and the reaction does not proceed any more. For example, the fermentation of the saccharide containing glucose as a main component with the microorganism is performed at 30° C. to 38° C. for about 1 to 5 days.

In the method for producing ethanol according to this embodiment, an additive solution containing at least acetic acid, formic acid, furfural, and hydroxymethylfurfural to the saccharide containing glucose as a main component to prepare a mixed solution containing the saccharide containing glucose as a main component and the additive solution, and a microorganism is added to the mixed solution to ferment the saccharide containing glucose as a main component using the microorganism. Thus, the production efficiency of ethanol can be improved compared with the case where the additive solution is not added. Furthermore, a solution produced as a result of the pretreatment of biomass and separated and removed from the pretreated biomass is used as the additive solution containing at least acetic acid, formic acid, furfural, and hydroxymethylfurfural. Thus, the disposal amount of the substance containing at least acetic acid, formic acid, furfural, and hydroxymethylfurfural, which has been treated as a liquid waste, can be decreased.

Second Embodiment

In this embodiment, the description will be made for the case where the saccharide is sucrose contained in a sugarcane juice.

In this embodiment, the additive solution containing at least acetic acid, formic acid, furfural, and hydroxymethylfurfural is added to a saccharide obtained by squeezing sugarcane and containing sucrose as a main component to prepare a mixed solution containing the saccharide containing sucrose as a main component and the additive solution (mixed solution-preparing step).

In this mixed solution-preparing step, the saccharide containing sucrose as a main component and an appropriate amount of the additive solution containing at least acetic acid, formic acid, furfural, and hydroxymethylfurfural, which is suitable for fermentation of the saccharide containing sucrose as a main component, are charged into a reaction vessel to mix the saccharide containing sucrose as a main component and the additive solution.

The mixing ratio of the acetic acid, formic acid, furfural, and hydroxymethylfurfural contained in the additive solution is preferably equal to that in the first embodiment.

The total concentration of the acetic acid, formic acid, furfural, and hydroxymethylfurfural contained in the mixed solution containing the saccharide containing sucrose as a main component and the additive solution is preferably 400 ppm to 4500 ppm and more preferably 1000 ppm to 4500 ppm.

The saccharide containing sucrose as a main component and the additive solution are stirred with a stirring blade or the like.

Subsequently, a microorganism is added to the mixed solution to ferment the saccharide containing sucrose as a main component in the mixed solution using the microorganism, thereby producing ethanol (fermentation step).

In this fermentation step, the mixed solution and an appropriate amount of the microorganism suitable for fermentation of the saccharide containing sucrose as a main component are charged into a reaction vessel to mix the mixed solution and the microorganism.

The microorganism used is the same as that in the first embodiment.

The amount of the microorganism added to the mixed solution is preferably 0.1 to 3 parts by mass and more preferably 0.2 to 2.2 parts by mass when the amount of the saccharide containing sucrose as a main component in the mixed solution is assumed to be 100 parts by mass.

The mixed solution and the microorganism are stirred with a stirring blade or the like.

In this fermentation step, the temperature of the mixture containing the microorganism is preferably adjusted so that the microorganism actively works. Specifically, the temperature is kept at 30° C. to 38° C.

The fermentation step is performed until the fermentation of the saccharide containing sucrose as a main component with the microorganism sufficiently proceeds and the reaction does not proceed any more. For example, the fermentation of the saccharide containing sucrose as a main component with the microorganism is performed at 30° C. to 38° C. for about 1 to 2 days.

In the method for producing ethanol according to this embodiment, an additive solution containing at least acetic acid, formic acid, furfural, and hydroxymethylfurfural is added to the saccharide containing sucrose as a main component to prepare a mixed solution containing the saccharide containing sucrose as a main component and the additive solution, and a microorganism is added to the mixed solution to ferment the saccharide containing sucrose as a main component using the microorganism. Thus, the production efficiency of ethanol can be improved compared with the case where the additive solution is not added.

EXAMPLES

Hereafter, the present invention will be further specifically described based on Examples and Comparative Examples, but the present invention is not limited to Examples below.

Example 1

Bagasse was subjected to a steam explosion treatment.

Subsequently, a substance containing at least acetic acid, formic acid, furfural, and hydroxymethylfurfural was separated and removed from the steam-exploded bagasse, and the substance was collected.

A slurry containing bagasse was prepared by dispersing 30 g of steam-exploded bagasse in 100 mL of water. The content of the bagasse in the prepared slurry was 30 w/v %.

Subsequently, the bagasse contained in the biomass slurry was degraded using cellulase under the following conditions to obtain a solution containing the saccharide containing glucose as a main component.

Weight of bagasse: 30 g-dry
Amount of cellulase added: 4 mg/g-substrate
Amount of solution: 100 mL
Temperature: 50° C.
pH: 5

Subsequently, the substance (additive solution) separated and removed from the bagasse and containing at least acetic acid, formic acid, furfural, and hydroxymethylfurfural was added to the solution containing the saccharide to mix the aqueous solution and the substance containing at least acetic acid, formic acid, furfural, and hydroxymethylfurfural. Thus, an aqueous solution (mixed solution) containing the saccharide containing glucose as a main component and the substance containing at least acetic acid, formic acid, furfural, and hydroxymethylfurfural was prepared. Herein, the total concentration of the acetic acid, formic acid, furfural, and hydroxymethylfurfural contained in the mixed solution was 2510 ppm.

Subsequently, yeast was added to the mixed solution to ferment the saccharide containing glucose as a main component in the mixed solution using the yeast, thereby producing ethanol. In this step of fermenting the saccharide containing glucose as a main component, the temperature of the mixed solution was kept at 34° C., and the concentrations of the glucose and ethanol contained in the mixed solution were measured over time from the start of fermentation. FIG. 1 illustrates the results.

Comparative Example 1

Ethanol was produced by fermenting the saccharide containing glucose as a main component in the same manner as in Example 1, except that the substance (additive solution) containing at least acetic acid, formic acid, furfural, and hydroxymethylfurfural was not added to the aqueous solution containing the saccharide containing glucose as a main component.

The concentrations of the glucose and ethanol contained in the aqueous solution were measured over time from the start of fermentation of the saccharide containing glucose as a main component. FIG. 1 illustrates the results.

It was found from the results in FIG. 1 that the ethanol production rate in Example 1 in which the substance containing at least acetic acid, formic acid, furfural, and hydroxymethylfurfural was added to the aqueous solution containing the saccharide containing glucose as a main component and the saccharide containing glucose as a main component was fermented with yeast was increased by 30% or more compared with Comparative Example 1 in which the substance containing at least acetic acid, formic acid, furfural, and hydroxymethylfurfural was not added to the aqueous solution containing the saccharide containing glucose as a main component and the saccharide containing glucose as a main component was fermented with yeast.

Example 2

Sugarcane was squeezed to prepare an aqueous solution containing 180 g/L of a saccharide containing sucrose as a main component.

Subsequently, an additive solution containing at least acetic acid, formic acid, furfural, and hydroxymethylfurfural was added to the aqueous solution to mix the aqueous solution and the substance containing at least acetic acid, formic acid, furfural, and hydroxymethylfurfural. Thus, an aqueous solution (mixed solution) containing the saccharide containing sucrose as a main component and the additive solution containing at least acetic acid, formic acid, furfural, and hydroxymethylfurfural was prepared. Herein, the total concentration of the acetic acid, formic acid, furfural, and hydroxymethylfurfural contained in the mixed solution was 2303 ppm.

Figure 2:
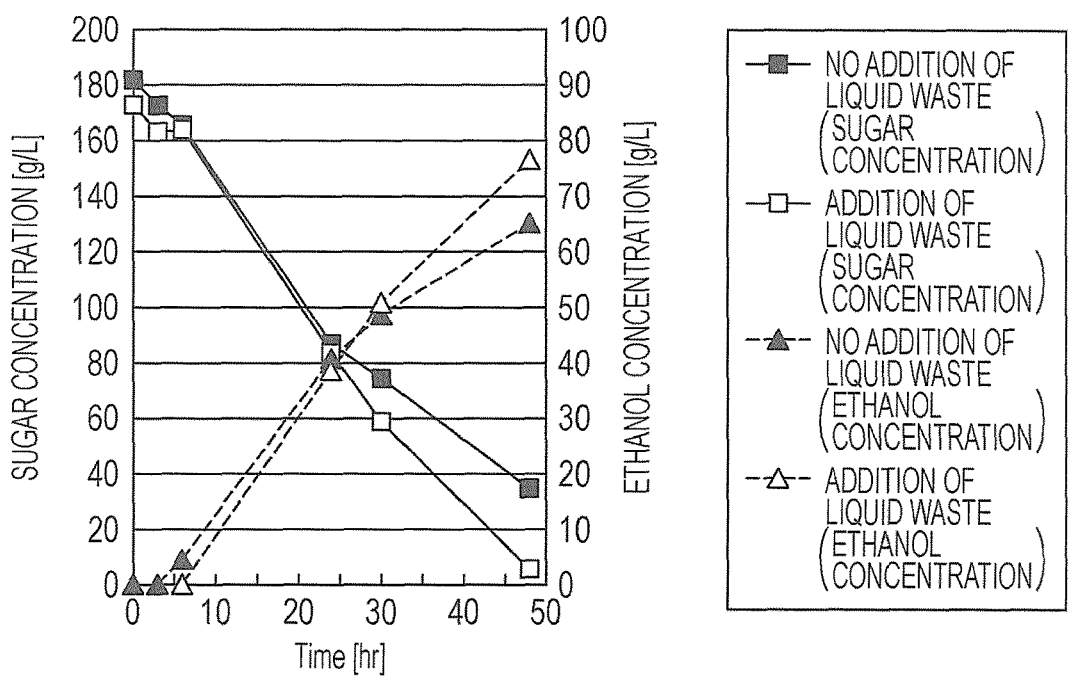
FIG. 2 is a graph illustrating the concentrations of sucrose and ethanol contained in a mixed solution (aqueous solution), the concentrations being plotted against the time elapsed from the start of fermentation in a step of fermenting a saccharide containing sucrose as a main component.

Subsequently, yeast was added to the mixed solution to ferment the saccharide containing sucrose as a main component in the mixed solution using the yeast, thereby producing ethanol. In this step of fermenting the saccharide containing sucrose as a main component, the temperature of the mixed solution was kept at 34° C., and the concentrations of the sucrose and ethanol contained in the mixed solution were measured over time from the start of fermentation. FIG. 2 illustrates the results.

Comparative Example 2

Ethanol was produced by fermenting the saccharide containing sucrose as a main component in the same manner as in Example 2, except that the additive solution containing at least acetic acid, formic acid, furfural, and hydroxymethylfurfural was not added to the aqueous solution containing the saccharide containing sucrose as a main component.

The concentrations of the sucrose and ethanol contained in the aqueous solution were measured over time from the start of fermentation of the saccharide containing sucrose as a main component. FIG. 2 illustrates the results.

It was found from the results in FIG. 2 that the ethanol production rate in Example 2 in which the additive solution containing at least acetic acid, formic acid, furfural, and hydroxymethylfurfural was added to the aqueous solution containing the saccharide containing sucrose as a main component and the saccharide containing sucrose as a main component was fermented with yeast was increased by 20% or more compared with Comparative Example 2 in which the additive solution containing at least acetic acid, formic acid, furfural, and hydroxymethylfurfural was not added to the aqueous solution containing the saccharide containing sucrose as a main component and the saccharide containing sucrose as a main component was fermented with yeast.

Experimental Example

Sugarcane was squeezed to prepare aqueous solutions containing 100 g/L to 200 g/L of a saccharide containing sucrose as a main component.

Subsequently, an additive solution containing at least acetic acid, formic acid, furfural, and hydroxymethylfurfural was added to each of the aqueous solutions to mix the aqueous solution and the substance containing at least acetic acid, formic acid, furfural, and hydroxymethylfurfural. Thus, an aqueous solution (mixed solution) containing the saccharide containing sucrose as a main component and the additive solution containing at least acetic acid, formic acid, furfural, and hydroxymethylfurfural was prepared. Herein, the total concentration of the acetic acid, formic acid, furfural, and hydroxymethylfurfural contained in the mixed solution was 217 ppm to 6680 ppm.

Subsequently, yeast was added to the mixed solution to ferment the saccharide containing sucrose as a main component in the mixed solution using the yeast, thereby producing ethanol. In this step of fermenting the saccharide containing sucrose as a main component, the temperature of the mixed solution was kept at 34° C., and the time required until the concentration of ethanol reached a predetermined concentration was measured.

Furthermore, yeast was added to each of the aqueous solutions containing 100 g/L to 200 g/L of the saccharide containing sucrose as a main component without adding the additive solution. The saccharide containing sucrose as a main component in the aqueous solution containing saccharide containing sucrose as a main component was fermented using the yeast to produce ethanol. In this step of fermenting the saccharide containing sucrose as a main component, the temperature of the solution containing the saccharide containing sucrose as a main component was kept at 34° C., and the time required until the concentration of ethanol reached a predetermined concentration was measured.

The ratio of the time required until the concentration of ethanol reached a predetermined concentration in the case where the additive solution was added to the aqueous solution containing the saccharide containing sucrose as a main component relative to the time required until the concentration of ethanol reached a predetermined concentration in the case where the additive solution was not added to the aqueous solution containing the saccharide containing sucrose as a main component was calculated. The calculated result was defined as an improvement ratio (%) of the ethanol production rate in the case where the additive solution was added to the aqueous solution containing the saccharide containing sucrose as a main component relative to the ethanol production rate in the case where the additive solution was not added to the aqueous solution containing the saccharide containing sucrose as a main component. Table 1 and FIG. 3 show the results.

TABLE 1

| Experimental Example | Total concentration of acetic acid, formic acid, furfural, and hydroxymethylfurfural added (ppm) | Improvement ratio of ethanol production rate (%) |
| --- | --- | --- |
| A | 2740 | 43 |
| B | 4500 | 57 |
| C | 1110 | 33 |
| D | 1028 | 33 |
| E | 787 | 25 |
| F | 581 | 22 |
| G | 400 | 20 |
| H | 217 | 5 |
| I | 5100 | −22 |
| J | 4700 | 5 |
| K | 6630 | −35 |

Figure 3:
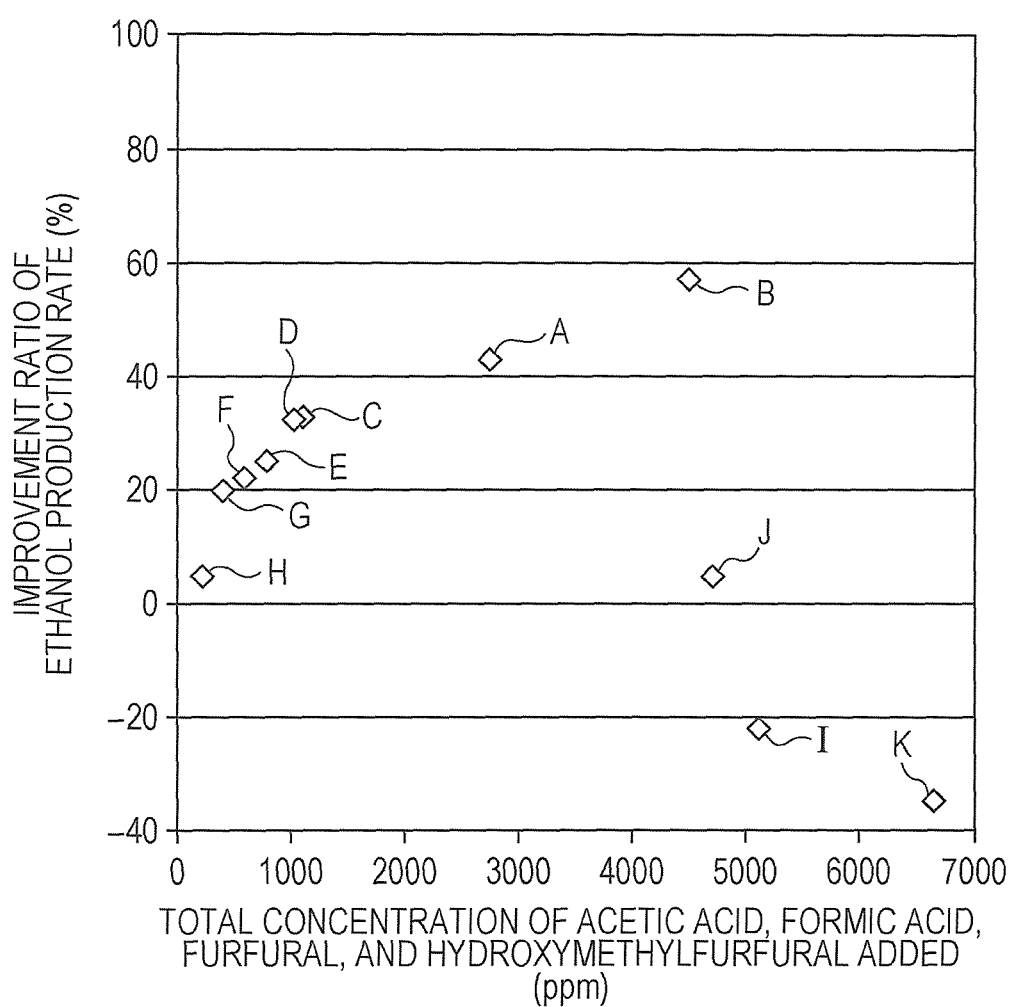
FIG. 3 is a graph illustrating an improvement ratio of the ethanol production rate in the case where an additive solution is added to an aqueous solution containing a saccharide containing sucrose as a main component relative to the ethanol production rate in the case where the additive solution is not added to the aqueous solution containing a saccharide containing sucrose as a main component.

It was found from the results in Table 1 and FIG. 3 that when the total concentration of the acetic acid, formic acid, furfural, and hydroxymethylfurfural added to the aqueous solution containing the saccharide containing sucrose as a main component was in the range of 400 ppm to 4500 ppm, the improvement ratio of the ethanol production rate was 20% or more.

The invention claimed is:

1. A method for producing ethanol with a saccharide obtained from a biomass, comprising:
   (a) performing a pretreatment process to the biomass;
   (b) removing a solution comprising acetic acid, formic acid, furfural, and hydroxymethylfurfural from the pretreated biomass;
   (c) dispersing the pretreated biomass in water to form a biomass slurry;

(d) obtaining the saccharide by degrading cellulose and/or hemicellulose contained in the biomass slurry using a cellulase and/or a hemicellulase;

(e) adding the solution comprising acetic acid, formic acid, furfural, and hydroxymethylfurfural to the saccharide;

(f) preparing a mixed solution comprising the saccharide and the solution of (e), wherein a total concentration of the acetic acid, the formic acid, the furfural, and the hydroxymethylfurfural contained in the mixed solution is 1000 ppm to 4500 ppm; and (g) adding a microorganism to the mixed solution to ferment the saccharide with the microorganism, thereby producing ethanol, wherein the microorganism is yeast, and wherein the biomass is selected from the group consisting of wood, grass, and agricultural residues.

2. The method for producing ethanol of claim 1, wherein the solution of (e) is a liquid waste produced by performing a steam explosion treatment or a dilute sulfuric acid treatment on the biomass.

\* \* \* \* \*